United States Patent
Choi et al.

(10) Patent No.: US 8,483,819 B2
(45) Date of Patent: Jul. 9, 2013

(54) MODULATOR OF VASCULAR PERMEABILITY USING PULSED LASER AND METHOD FOR MODULATING VASCULAR PERMEABILITY USING THE SAME

(75) Inventors: Chulhee Choi, Daejeon (KR); Myunghwan Choi, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 155 days.

(21) Appl. No.: 12/785,155

(22) Filed: May 21, 2010

(65) Prior Publication Data
US 2011/0152744 A1 Jun. 23, 2011

(30) Foreign Application Priority Data

Dec. 17, 2009 (KR) .......................... 10-2009-0126311

(51) Int. Cl.
*A61N 1/30* (2006.01)
*A61B 18/18* (2006.01)
*A61N 1/04* (2006.01)

(52) U.S. Cl.
CPC .................................... *A61N 1/0448* (2013.01)
USPC ................................................ 604/20; 606/2

(58) Field of Classification Search
CPC ..................................................... A61N 1/0448
USPC .......... 606/2, 3, 4, 10, 11, 13–17; 604/19–21
See application file for complete search history.

(56) References Cited

U.S. PATENT DOCUMENTS

| | | | |
|---|---|---|---|
| 6,251,099 B1 | 6/2001 | Kollias et al. | |
| 6,424,863 B1 | 7/2002 | Flock et al. | |
| 7,258,687 B2 | 8/2007 | Friedman et al. | |
| 2012/0203103 A1* | 8/2012 | Wang et al. | 600/431 |

OTHER PUBLICATIONS

Nozomi Nishimura et al. (2006) "Targeted insult to subsurface cortical blood vessels using ultrashort laser pulses: three models of stroke," Nature Methods, 3:2: 99-108.

Hua-Tai Xu et al. (2007) "Choice of cranial window type for in vivo imaging affects dendritic spine turnover in the cortex," Nature Neuroscience, 10:5: 549-551.

* cited by examiner

*Primary Examiner* — Huy K Mai
(74) *Attorney, Agent, or Firm* — Lathrop & Gage LLP

(57) ABSTRACT

Disclosed herein is a modulator of vascular permeability using pulsed laser and a method for modulating vascular permeability using the same. More specifically, because the pulsed laser effectively induces vascular permeabilization, effectively delivers intravascular materials into tissues and minimizes insult to the tissues by the induced vascular permeabilization, and locally targets a subcutaneous tissue for noninvasive modulation due to its nonlinearity, it may be usefully used for modulation of permeability.

11 Claims, 8 Drawing Sheets

MODULATOR OF VASCULAR PERMEABILITY USING PULSED LASER AND METHOD FOR MODULATING VASCULAR PERMEABILITY USING THE SAME

CROSS-REFERENCES TO RELATED APPLICATION

This patent application claims the benefit of priority from Korean Patent Application No. 10-2009-0126311, filed on Dec. 17, 2009, the contents of which are incorporated herein by reference.

BACKGROUND OF THE INVENTION

1. Field of the Invention

The present disclosure relates to a modulator of vascular permeability using a pulsed laser and a method for modulating vascular permeability using the same.

2. Description of the Related Art

Because a drug administered into the blood vessel must cross the vascular wall to reach a desired target, vascular permeability has become a major consideration in drug development. In particular, in the case of an organ such as brain or retina in which a blood-brain barrier or blood-retina barrier is present, most drug candidates cannot cross the vascular wall, which has been a major constraint for drug development. Thus, a drug delivery system, with which a drug may cross the vascular wall effectively, is required.

In order to circumvent inefficiency problems related to drug delivery through permeation of the vascular wall, various methods have been suggested. Transcranial delivery is an approach that drills a hole in the skull and injects drugs intracerebrally or intracerebroventricularly. This method is viewed as a novel target route being developed for central nervous system drugs, but is disadvantageous in that it is very invasive. Furthermore, transnasal delivery is an approach to traverse the nasal mucosal barrier and inject drugs, but is limited only to low-molecular weight lipid soluble drugs. In addition, although there is an approach to chemically modify drugs and inject them, such as enhancing lipid solubility and lowering molecular weight, or taking advantage of an endogenous transporter-mediated process, there is no method that allows non-invasive and local delivery of high-molecular weight drugs into a target region.

A laser light source is one that emits photons in a coherent light beam. A typical laser is a monochromatic color, i.e., it has only one wavelength or color. Most light sources emit a large number of incoherent lights waves across a broad wavelength spectrum over a wide area. However, a laser beam is generally thin, and does not diffuse. In addition to its uses duet to its intrinsic light characteristics, the applications of laser have been extended to various areas such as industry, medical care, nuclear fusion, instrumentation, information memory, and optical communications. Lasers may be largely classified into pulsed and continuous wave types. When laser transition occurs not so much continuously but simultaneously, laser lasts for a short time and becomes a pulsed laser. While a continuous wave laser is used to continuously produce high heat, a pulsed laser is used when a strong and instantaneous energy burst is required.

In particular, near-infrared femtosecond pulsed lasers have been widely used for in vivo imaging due to their deep tissue penetration, reduced scattering, and localized nonlinear absorption. These advantages have also allowed for various optical modulations of live cells and tissues in a living animal, such as production of intracellular calcium, dissection of intracellular organelles, gene transformation, construction of a stroke animal model, acceleration of nerve firing, and blood flow inhibition. Methods for constructing an animal model of blood vessel rupture have been reported (N, Nishimura, et al., *Nature methods*, 2006, vol. 3, no. 2, pp. 99-108). Irradiation of an amplified 1 KHz pulsed laser can induce targeted insult to the cerebral cortical vascular wall, such as hemorrhage, intravascular clot formation or vascular extravasation, and laser induced vascular extravasation resulted in insult to the blood brain barrier (BBB). A method for disrupting a target blood vessel using an ultra-short pulsed laser (U.S. Pat. No. 7,258,687) and a method for administering a drug transdermally (U.S. Pat. No. 6,251,099) have been reported, but modulation of vascular permeability using an ultra-short pulsed laser has not been reported. Therefore, studies on optical modulation methods of vascular permeability, which are not accompanied by irreversible vascular damage, are needed.

Thus, the present inventors have studied an optical method for modulating vascular permeability to effectively deliver a drug in vivo into a target region, and confirmed that a device and a method for modulating vascular permeability may be usefully used to effectively deliver a material to be administered in vivo into a target region because a near-infrared femtosecond pulsed laser, which is low in heat loss with respect to tissues, non-invasive, and non-linear, effectively induces vascular permeability, thereby leading to completion of the present invention.

SUMMARY OF THE INVENTION

One object of the present invention is to provide a modulator of vascular permeability using a pulsed laser and a method for modulating vascular permeability using the same.

In order to achieve the object, the present invention provides a modulator of vascular permeability, including:

a pulsed laser generating unit configured to generate a pulsed laser;

a light energy transmitting unit extended from the generating unit to transmit the pulsed laser generated from the generating unit; and an irradiating unit installed at the end of the light energy transmitting unit to locally irradiate the pulsed laser on a target blood vessel.

The present invention also provides a method for modulating vascular permeability, the method including:

1) intravascularly injecting a material to be delivered into an individual;

2) targeting a vascular wall; and 3) irradiating a pulsed laser on the targeted blood vessel by using the modulator of vascular permeability.

Furthermore, the present invention provides a method for delivering a drug into a target tissue, including irradiating a pulsed laser on a blood vessel by using the modulator of vascular permeability.

BRIEF DESCRIPTION OF THE DRAWINGS

The above and other objects, features and other advantages of the present invention will be more clearly understood from the following detailed description taken in conjunction with the accompanying drawings, in which.

(a) photos of the cerebral cortical blood vessel taken by a two-photon fluorescence microscope over time, and white squares indicate regions of interest (scale bar; 100 µM);

(b) photos illustrating Z-projection images 5 minutes after laser irradiation; and (c) a graph illustrating a relative fluorescent unit (r.f.u.) over time in each region.

Figure 4:
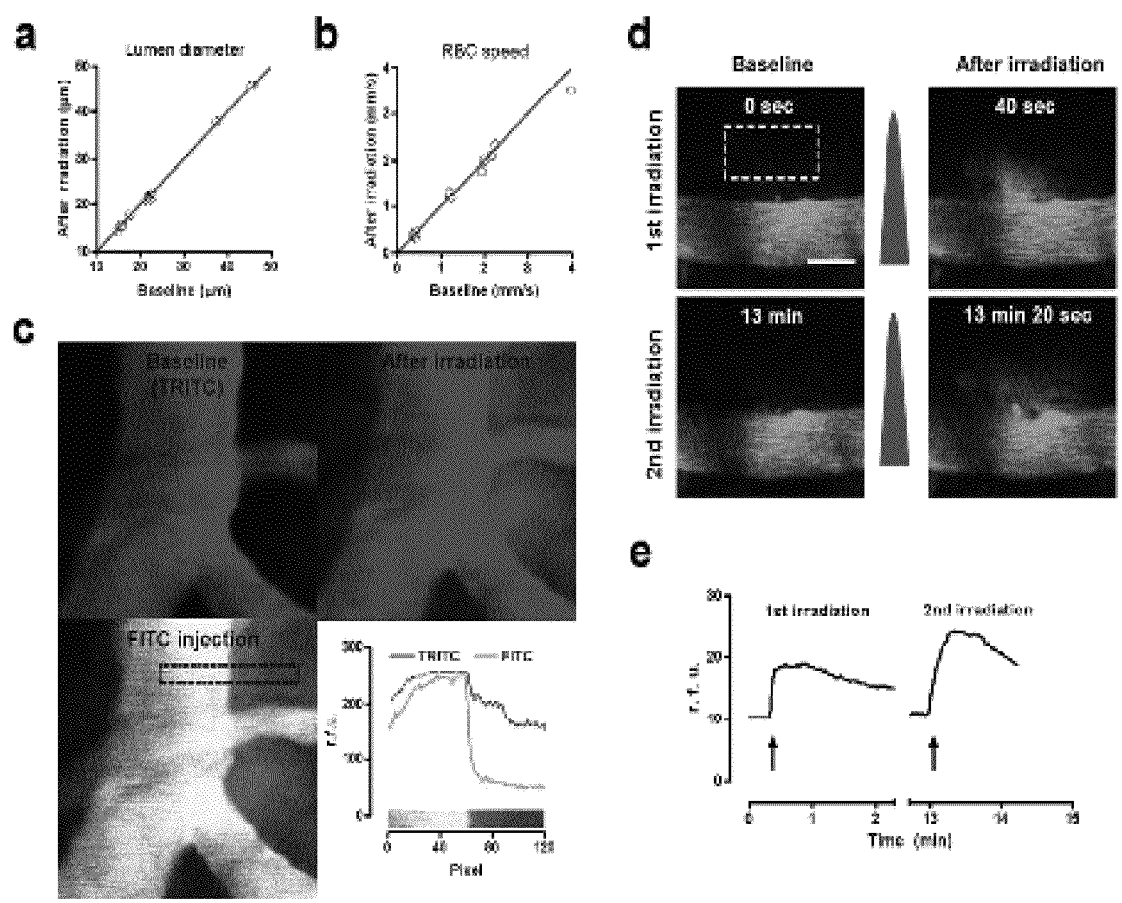

FIG. 4 is a group of photos and graphs illustrating minimal invasions by a femtosecond pulsed laser inducing vascular permeabilization in the brain of a mouse:

Each of (a) and (b) is a graph illustrating the structure of a blood vessel and the non-invasion of blood flow, respectively;

(c) a group of photos and a graph illustrating the integrity of the blood brain barrier. The upper left and right photos show the baseline blood vessel structure and the induction of extravasation after laser irradiation, respectively. The lower left and right photos show FITC-dextran injection for identification of the BBB integrity and distribution of the fluorescent probes in a region indicated with a dashed rectangle, respectively, 10 minutes after inducting extravasation; and (d, e) a group of photos and graphs illustrating repeatability on induction of vascular permeabilization. White dots in (d) indicate the region of laser irradiation, while arrows in (e) indicate the times of laser irradiation (scale bar; 20 µm).

Figure 5:
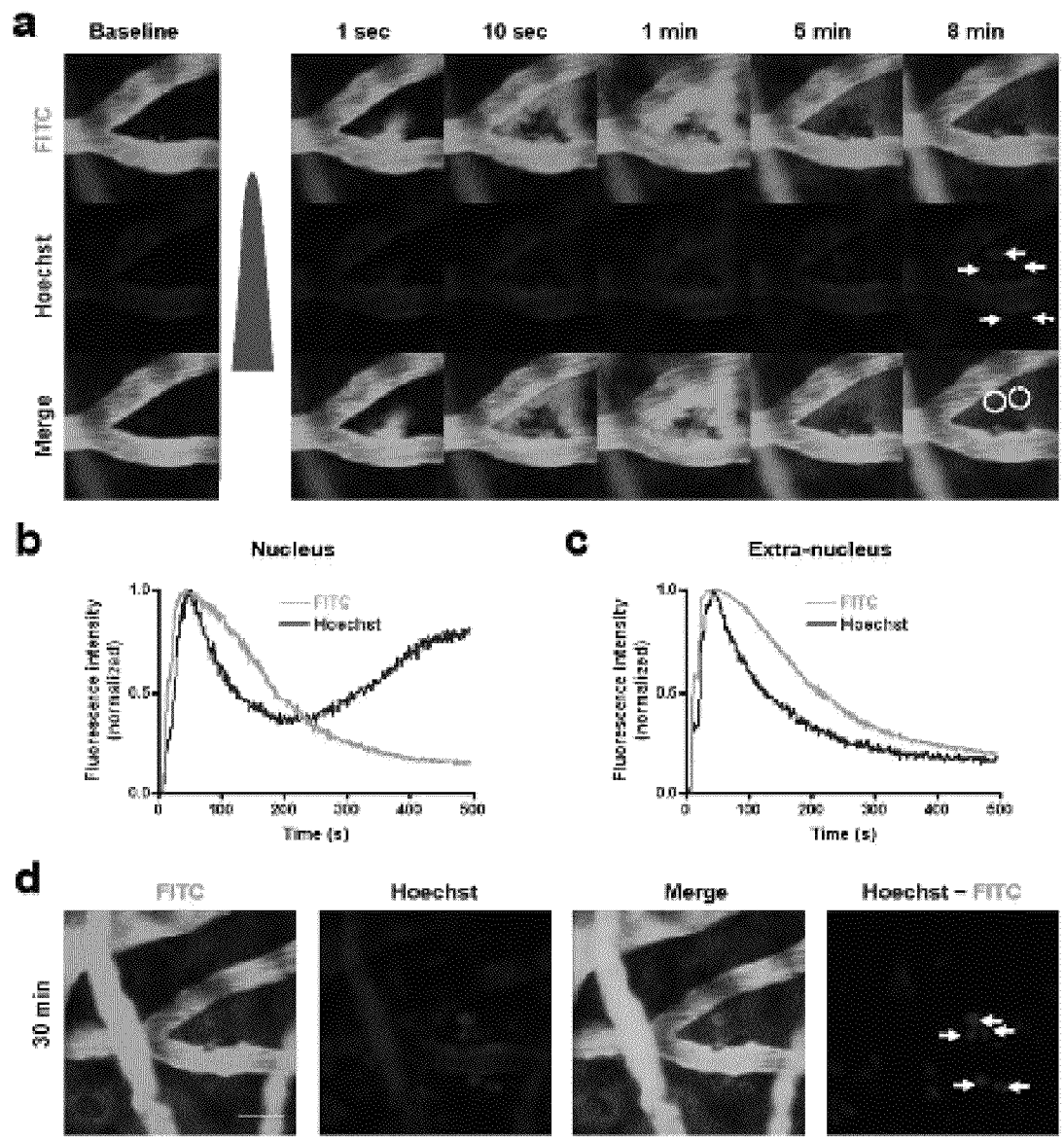

FIG. 5 is a group of photos and graphs illustrating the delivery of nucleus probe molecules (Hoechst) by pulsed laser induced vascular permeabilization:

(a) time-series photos of extravasation. A white dot indicates the region of laser irradiation;

(b, c) graphs illustrating distributions of the FITC-dextran and Hoechst in nucleus and extra-nucleus regions over time; and (d) a group of photos illustrating Local nucleus staining in the brain cortex taken 30 min after inducing extravasation. Arrows indicate the clear nuclear staining near the irradiated region (scale bar, 20 µm).

Figure 6:
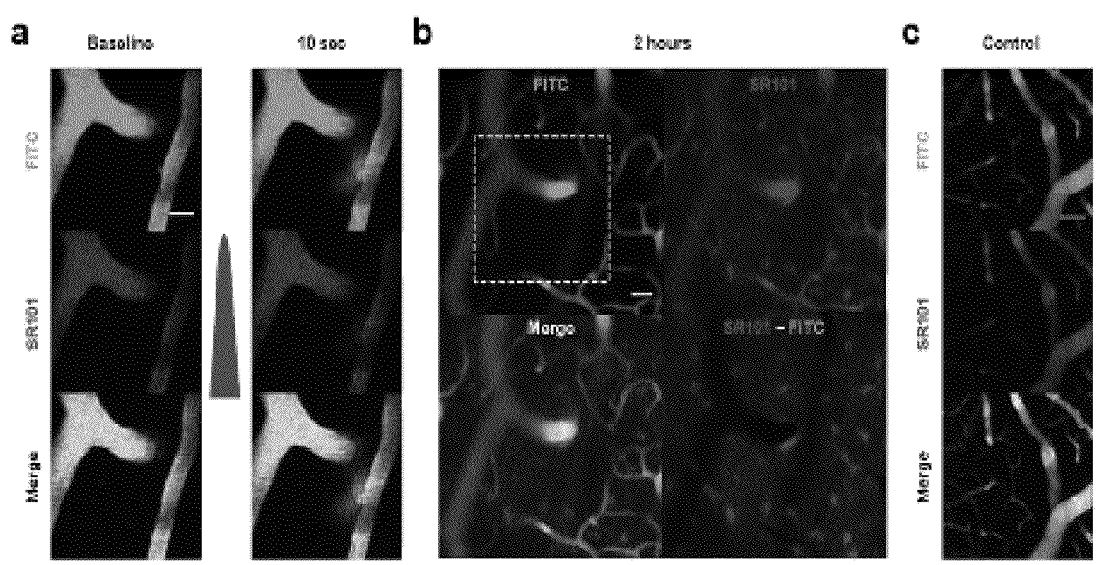

FIG. 6 is a group of photos illustrating the delivery of an astrocyte specific marker (SR101) by pulsed laser induced vascular permeabilization.

(a) time-series photos of extravasation. A white dot indicates the region of laser irradiation (scale bar; 20 µm);

(b) photos illustrating staining of astrocytes in the brain 2 hours after inducing extravasation. A white dashed box indicates the imaged region in (a) (scale bar; 50 µm);

(c) photos of controls groups not subjected to laser irradiation (scale bar; 50 µm).

Figure 7:
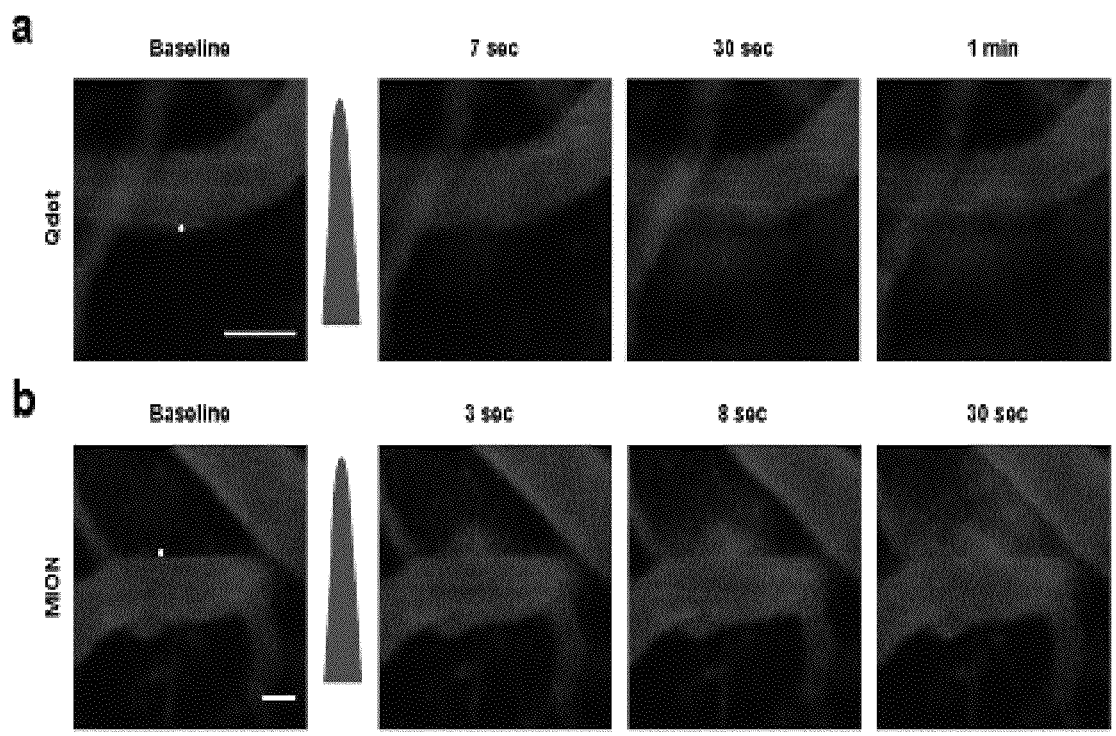

FIG. 7 is a group of photos illustrating the delivery of nano materials by pulsed laser induced vascular permeabilization:

(a) Quantum dot; and (b) TAMRA-conjugated magnetic oxide particles (MION).

Figure 8:
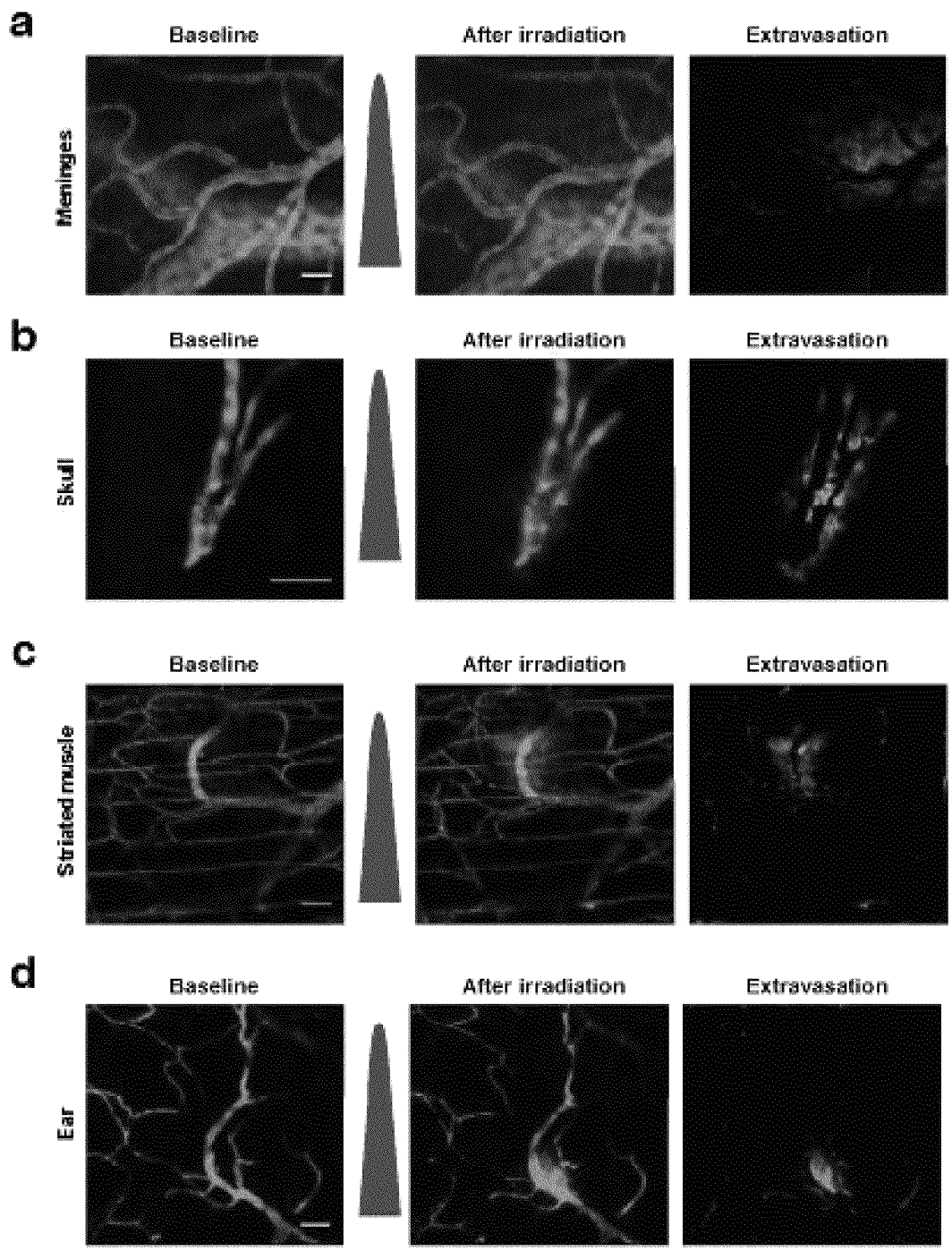

FIG. 8 is a group of photos illustrating pulsed laser induced vascular permeabilization in other tissues (scale bar; 50 µm):

(a) meningeal vasculature;

(b) skull vasculature;

(c) striated muscle in the dorsal skin; and (d) ear.

DESCRIPTION OF THE PREFERRED EMBODIMENTS

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, the present invention will be described in detail.

The present invention provides a modulator of vascular permeability using a pulsed laser.

The pulsed laser preferably includes, but is not limited to, a pulsed laser generating unit configured to generate a pulsed laser;

a light energy transmitting unit extended from the generating unit to transmit the pulsed laser generated from the generating unit; and an irradiating unit installed at the end of the light energy transmitting unit to locally irradiate the pulsed laser on a target blood vessel.

Figure 1:
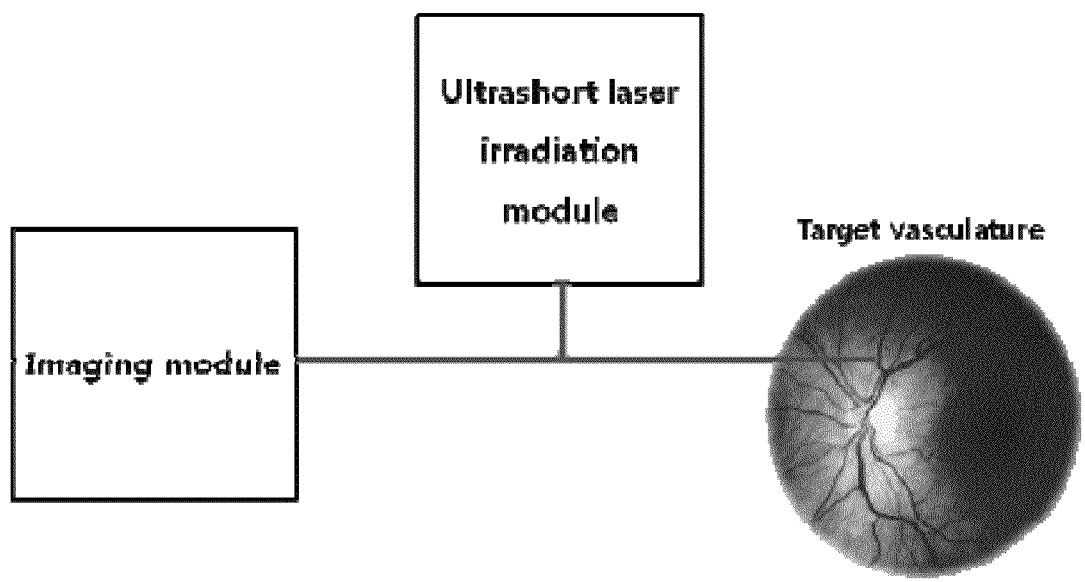
FIG. 1 is a schematic view illustrating a modulator of vascular permeability.
Figure 2:
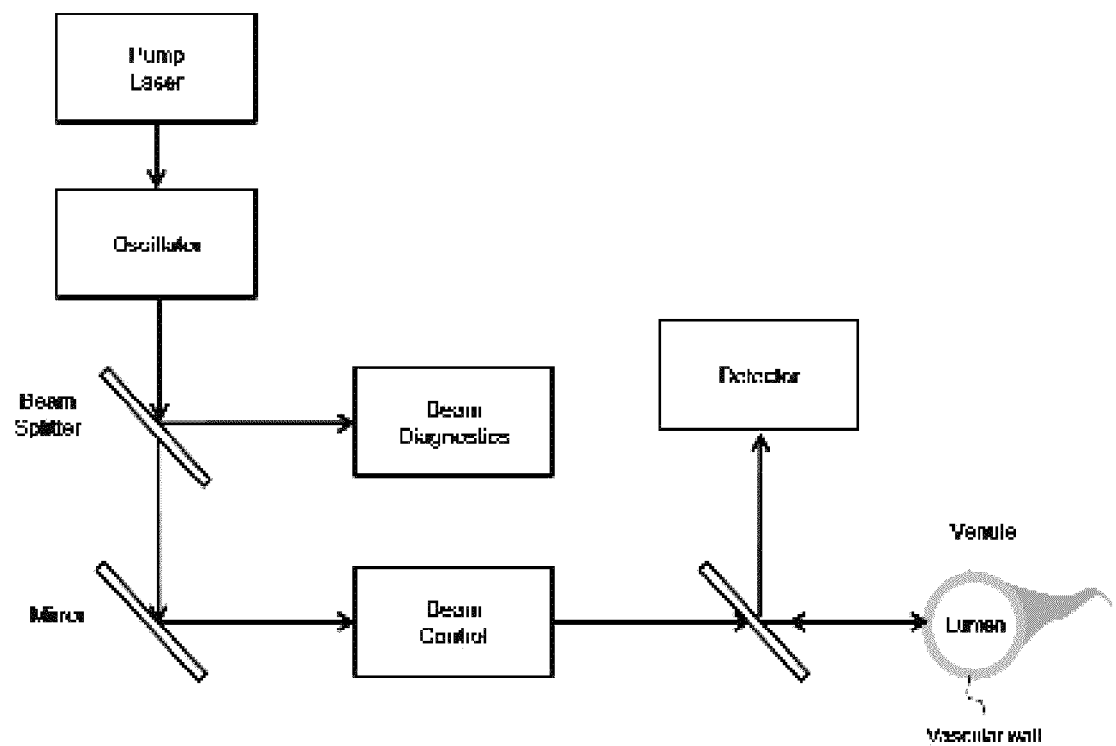
FIG. 2 is a view illustrating the structure of a modulator of vascular permeability.

As indicated in FIG. 2, the pulsed laser generating unit preferably includes, but is not limited to, a pump laser and an oscillator.

Preferably, the modulator of vascular permeability further includes, but is not limited to, a beam diagnostics (unit) mounted on the light energy transmitting unit to measure a pulsed laser generated from the generating unit.

Preferably, the modulator of vascular permeability additionally includes a beam control (unit) mounted on the light energy transmitting unit to control a pulsed laser generated from the generating unit. The beam control (unit) preferably controls, but is not limited to, laser intensity, irradiation time, irradiation mode, irradiation position, or irradiation sequence.

Preferably, the modulator of vascular permeability further includes, but is not limited to, a detector mounted on the light energy transmitting unit to detect a pulsed laser reflected from a target blood vessel.

Preferably, the light energy transmitting unit additionally includes, but is not limited to, a beam splitter to diffuse part of a pulsed laser generated from the generating unit, output it externally, and reflect the remainder into a beam diagnostics (unit), a reflection mirror to reflect light emitted from the beam splitter into the beam control (unit), or a reflection mirror to reflect light reflected from a target blood vessel into the detector.

Preferably, the modulator of vascular permeability further includes, but is not limited to, an imaging unit to photograph and show vascular permeabilization pattern images.

The modulator of vascular permeability may additionally include, but is not limited to, an injection inlet to inject a marker material for identification of a material to be intravascularly delivered and intravascular permeabilization into an individual, installed at the end of an irradiation unit. The marker material is preferably any one selected from the group consisting of, but not limited to, fluorescent material, phosphor, color former, luminescent material, MRI contrast agent, and radiotracer.

The pulse-width of the pulsed laser is preferably, but not limited to, about 1 femtosecond to about 100 nanoseconds. The wavelength of the pulsed laser is preferably, but not limited to, about 700 nm to about 1000 nm, which is a range that can achieve high tissue permeabilization. The repetition rate of the pulsed laser is preferably, but not limited to, about 1 MHz to about 100 MHz. The irradiance of the pulsed laser is preferably, but not limited to, a multiphoton ionization threshold to an optical breakdown threshold, of a target tissue. In addition, the irradiation duration by the pulsed laser is preferably, but not limited to, about 100 ns to about 10 ms.

The blood vessel is preferably one present in at least one selected from the group consisting of, but not limited to, the brain, retina, meningeal vasculature, skull vasculature, striated muscle in the dorsal skin, and ear.

Figure 3:
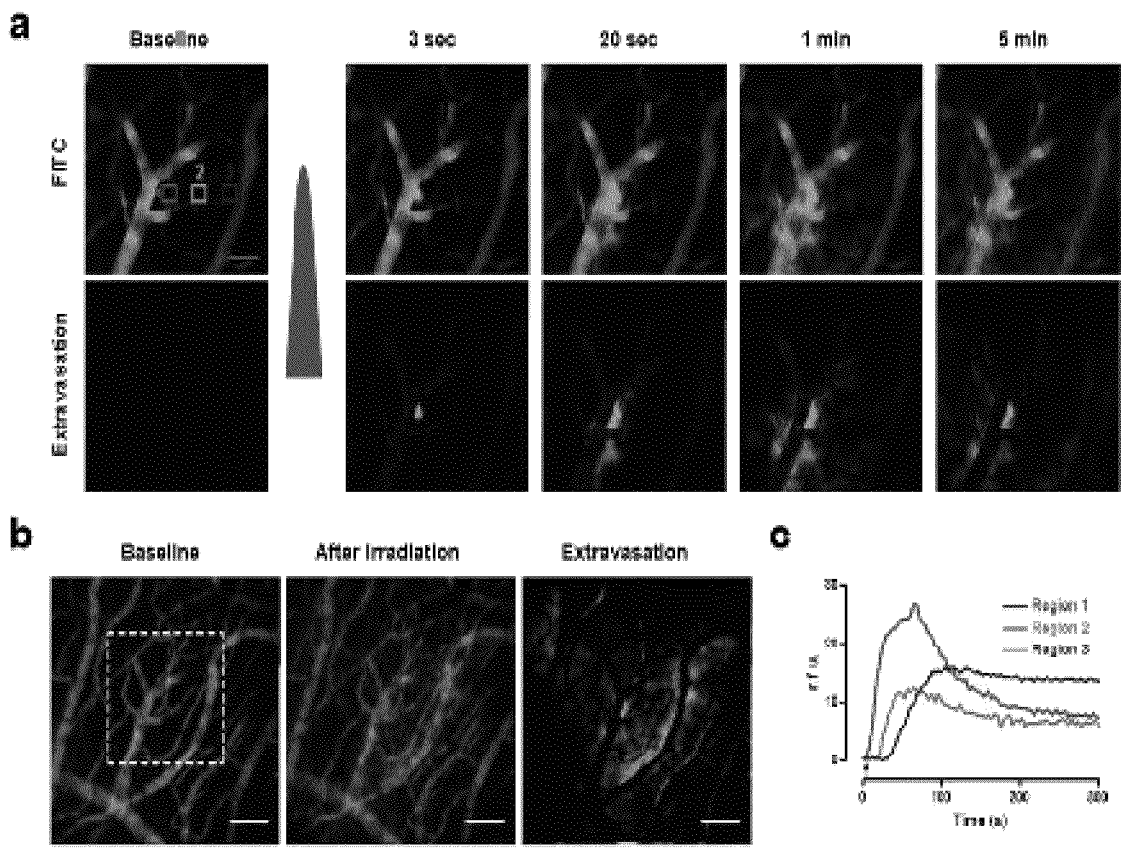
FIG. 3 is a group of photos and a graph illustrating vascular permeabilization in the brain of a mouse induced by a femtosecond pulsed laser.

In order to confirm pulsed laser induced vascular permeabilization in the blood vessel, the present inventors irradiated pulsed laser on cerebral cortical vein of a thinned skull model mouse. As a result, vascular permeabilization was induced by the irradiation of pulsed laser, and it was confirmed that 2M-Da dextran-conjugated FITC fluorescent probe molecules which do not cross the vascular wall without stimulation were transiently extravasated into the brain tissue around the vascular wall (See FIG. 3).

It was confirmed that these pulsed laser irradiations on the blood vessel brought about no changes in lumen diameter, blood flow, and blood brain barrier, resulting in no damage to the blood vessel (See FIGS. 4a, 4b, and 4c). When a pulsed laser was repeatedly irradiated, vascular permeabilization was shown to be reversibly induced with repeatability (See FIGS. 4d and 4e).

In order to confirm whether materials were intravascularly delivered into tissues by pulsed laser, the present inventors injected nucleus-specific probes (Hoechst), astrocyte-specific probes (sulforhodamine 101, SR101), and nanomaterials (Quantum dot and TAMRA-conjugated MiON) into the blood vessel and irradiated pulsed laser on the vessel. As a result, intravascular probes were extravasated into the brain tissue, leading to observation of nuclei or astrocytes dyed with fluorescent probes in the tissue around the blood vessel (See FIGS. 5 and 6), and it was confirmed that nanomaterials were also extravasated from the vascular wall and distributed around the blood vessel (See FIG. 7). Thus, it can be seen that materials in the blood are delivered into a target tissue by pulsed laser irradiation.

In order to confirm the induction of vascular permeabilization in the blood vessel in various tissues by pulsed laser, the present inventors irradiated pulsed laser on meningeal vasculature, skull vasculature, striated muscle in the dorsal skin, and ear of a mouse. As a result, it was confirmed that fluorescent materials were extravasated into the blood vessel of various tissues other than the brain tissue (See FIG. 8).

Therefore, it can be seen that pulsed laser may be usefully used as a component of a device for modulation of vascular permeability.

The present invention also provides a method for modulating vascular permeability, including irradiating pulsed laser on the blood vessel by using the modulator of vascular permeability.

Specifically, the present invention provides a method for modulating vascular permeability, including:

1) intravascularly injecting a material to be delivered into an individual;

2) targeting a vascular wall; and 3) irradiating a pulsed laser on the targeted blood vessel by using the modulator of vascular permeability.

In the method, the individual in 1) is human or vertebrate, preferably human or mammal, more preferably human, or experimental animal such as rat, rabbit, guinea pig, hamster, dog, and cat, and most preferably human, or anthropoid such as chimpanzee and gorilla.

In the method, it is desirable to inject both the material to be delivered in 1) and a marker material for identification of vascular permeabilization, and the marker material is preferably any one selected from the group consisting of, but not limited to, fluorescent material, phosphor, color former, luminescent material, MRI contrast agent, and radiotracer.

In the method, the vascular wall in 2) is preferably targeted by any one selected from the group consisting of, but not limited to, confocal fluorescent imaging, multiphoton fluorescent imaging, and optical coherence tomography.

In the method, the blood vessel in 3) is preferably one present in at least one selected from the group consisting of, but not limited to, the brain, retina, meningeal vasculature, skull vasculature, striated muscle in the dorsal skin, and ear.

In the method, the pulse-width of the pulsed laser in 3) is preferably, but not limited to, about 1 femtosecond to about 100 nanoseconds. The wavelength of the pulsed laser is preferably, but not limited to, about 700 nm to about 1000 nm, which is a range that can achieve high tissue permeabilization. The repetition rate of the pulsed laser is preferably, but not limited to, about 1 MHz to about 100 MHz. The irradiance of the pulsed laser is preferably, but not limited to, a multiphoton ionization threshold to an optical breakdown threshold, of a target tissue. In addition, the irradiation duration by pulsed laser is preferably, but not limited to, about 100 ns to about 10 ms.

The method for modulating vascular permeability preferably includes observing physiological parameters, and the physiological parameters are preferably, but not limited to, changes in vivo such as degree of damage to blood vessel, blood flow, or vascular diameter.

The method for modulating vascular permeability preferably includes securing an optical accessibility to the blood vessel, and the securing of the optical accessibility preferably uses, but not limited to, 1 mm or less optical fiber.

In order to confirm the induction of vascular permeabilization by pulsed-laser, the present inventors irradiated pulsed-laser on the blood vessel. As a result, pulsed laser effectively induced vascular permeabilization. Because not only intravascular molecules by the induced vascular permeabilization may be effectively delivered into the tissue, but also non-invasive modulation is possible from the fact that a subcutaneous tissue may be transiently and locally targeted by the minimal tissue damage and the non-linearity, it can be seen that pulsed laser may be usefully used for modulation of vascular permeability.

The present invention also provides a method for delivering a drug into a target tissue, including irradiating pulsed laser on the blood vessel by using the modulator of vascular permeability.

The drug has stability in the blood without crossing the normal vascular wall, permeabilization is enabled in the vascular wall by the pulsed laser of the present invention, and extravasation into the tissue may be preferably confirmed, but is not limited thereto.

Specifically, the present invention may irradiate pulsed laser into a target vessel to induce a local vascular permeabilization and deliver intravascular materials locally into a tissue. Through such a material delivery, a certain drug may be usefully delivered into a desired local region. Through modulation of vascular permeability, the extravasation of intravascular drugs and materials into the tissue may be also modulated.

Thus, because the pulsed laser of the present invention induces vascular permeabilization, it can be seen that the laser is usefully used for drug delivery.

Hereinafter, the present invention will be described in more detail with reference to the following examples.

However, the following examples are provided for illustrative purposes only, and the scope of the present invention should not be limited thereto in any manner.

Example 1

Construction of a Thinned Skull Model Mouse

A thinned skull model was constructed according to a method described in a previous literature (H. T. Xu. et al., *Nat Neurosci* 10(5), 549-551, 2007) by using 7- to 10-week-old male ICR mice (Charles River Japan Inc, Yokohama, Japan). After anesthesia with an intraperitoneal injection of ketamine-xylazine, the scalp was removed and the skull was glued to a custom-designed metal plate (Namil Optical Components, Incheon, Korea), using dental cement. Using a high-speed micro-drill, a circular area of skull, 2-4 mm in diameter, over a region of interest was thinned under a dissection microscope until a thin, smooth preparation was achieved. The animal care and construction procedures were performed under the approval of the Animal Care Committee of KAIST (Daejeon, Republic of Korea).

Example 2

Identification of Pulsed Laser Induced Vascular Permeabilization

<2-1> Pulsed Laser Stimulation on Cerebral Cortical Vein

To observe the induction of vascular permeabilization by pulsed laser irradiation, pulsed laser was stimulated on a mouse cerebral cortical vein. Specifically, two-photon laser scanning microscopy (LSM510; Carl Zeiss, Oberkochen, Germany) with a femtosecond pulsed laser (Chameleon; Coherent, Santa Clara, Calif., USA) tuned to 800 nm and a water immersion objective lens (20×, 1.0 numerical aperture) was used. Target venules which coursed parallel to the cerebral cortical surface and which had lumen diameters of 10-50 µM and subsurface depths of up to 100 µM were selected in a thinned skull window model. The vascular type was measured by confirming the direction of blood flow in the branching vessels. To target the vascular wall, a region outside the visualized luminal surface was selected for irradiation. The irradiation duration was fixed at 1.6 ms. The average laser power was set initially at 300 mW and was increased up to 2000 mW, until extravasation was observed.

<2-2> Two-Photon Fluorescent Imaging Using Two-Photon Laser Scanning Microscopy

After pulsed laser was irradiated using the two-photon laser scanning microscopy in Example <2-1>, imaging processes were performed at predetermined times (3 sec, 20 sec, 1 min, and 5 min) to confirm the permeabilization in the cerebral cortical vein. 2M-Da FITC-dextran was intravenously injected, the mouse was placed on a frame custom-designed as a structure for minimizing the movement of an animal (Namil Optical Components, Incheon, Korea), and fluorescent imaging processes were performed. The average laser power used for imaging was about 90 mW or less.

ImageJ or MATLAB was used for all of the following image processing and data quantification, and TurboReg or StackReg function was used to eliminate the structure. Data were expressed as mean±standard error. Statistical analyses were performed using Graph Pad Prism software and data were expressed as mean±standard error. Statistical differences were analyzed by t-test where indicated. A value of $p<0.05$ was considered to be statistically significant.

As a result, it was confirmed that intravascular fluorescent materials were locally extravasated into substantial tissues around a target vascular wall (FIGS. 3a and 3b).

<2-3> Identification of Transient Increase of Vascular Permeability Through Measurement of Fluorescent Intensity Around a Target Region by Pulsed Laser Pulsed laser was irradiated according to the method in Example <2-1>, and fluorescent intensity was each measured in a region 3 around a target vascular wall for 300 sec after irradiation to observe the extravasation degree of fluorescent probes into the region.

As a result, the fluorescent intensity decreased progressively farther away from a central part of permeabilization, and thus it was confirmed that the fluorescent probes were diffused into tissues around the region. Accordingly, it could be seen that the increase of vascular permeability was a transient phenomenon by laser stimulation (FIG. 3c).

Example 3

Identification of Effects of Pulsed Laser Irradiation on Damage to Vascular Wall 3-1> Effects of Pulsed Laser Irradiation on Changes in a Target Blood Vessel In order to quantitatively analyze structural and functional changes of a target blood vessel by pulsed laser irradiation, changes in lumen diameter, blood flow, and BBB integrity were checked. According to the method in Example <2-1>, pulsed laser was irradiated on a target blood vessel, and the lumen diameter and blood flow in the blood vessel were measured as the baseline vascular structure and the red blood cell speed before and 10 minutes after induced extravasation. In addition, a 70 kDa dextran conjugated dye was used to check the BBB integrity. Extravasation was induced with red-colored 70 kDa TRITC-dextran and stood for about 10 min. Next, green-colored 70 kDa FITC-dextran was intravenously injected to check whether the BBB was restored.

As a result, it was shown that there were no changes in lumen diameter and blood flow by pulsed laser irradiation (FIGS. 4a and 4b) and secondly administered FITC-dextran resided in the vascular lumen, indicative of intact BBB (FIG. 4c).

<3-2> Effects of Repeated Pulsed Laser Irradiation on Induction of Vascular Permeabilization Pulsed laser was repeatedly irradiated on a target blood vessel according to the method in Example <2-1> to see the repeatability of pulsed laser induced vascular permeabilization. 13 min after pulsed laser was irradiated, the same or a little stronger power pulsed laser was repeatedly irradiated on the same target position.

As a result, it was confirmed that extravasation was repeatedly induced in the blood vessel as pulsed laser was repeatedly irradiated (FIGS. 4d and 4e). It could be seen that a femtosecond pulsed laser minimally caused insult to the blood vessel and reversibly induces vascular permeabilization.

Example 4

Identification of Noninvasive Delivery of Small Molecules by Pulsed Laser Irradiation 4-1> Delivery of Probe Molecules into the Brain Tissue to Target a Nucleus In order to confirm whether intravascular materials may be delivered into a tissue by pulsed laser induced vascular permeabilization, the present inventors checked whether probes staining nuclei in the blood vessel may be delivered into a tissue by pulsed laser irradiation. Hoechst 333342 as a nuclear staining probe and 2M-Da FITC-dextran as a plasma marker were intravenously injected, and pulsed laser was irradiated according to the method in Example <2-1>. Fluorescence of Hoechst 333342 and 2M-Da FITC-dextran was analyzed at a predetermined time after the laser irradiation.

As a result, it was shown that fluorescent probes were delivered into a substantial tissue around the brain (FIGS. 5a and 5c). Approximately 5 min after laser irradiation, accumulation of Hoechst signal was visible as ring shaped structures in the brain tissue and became solid circles over time with brighter fluorescence, indicating progressive binding to nuclei (FIGS. 5a and 5b). The FITC-dextran image could be subtracted from the Hoechst image to selectively visualize the nuclei stained with Hoechst (FIG. 5d). Accordingly, it could be seen through identification of nuclear staining in the brain tissue by Hoechst that intravascular molecules could be delivered into the tissue by pulsed laser induced vascular permeabilization.

<4-2> Delivery of Probe Molecules into the Brain Tissue to Target an Astrocyte

In order to see whether probes staining astrocytes present in the blood vessel may be delivered into a tissue by pulsed laser irradiation, sulforhodamine 101(SR101) as a astrocyte staining probe and 2M-Da FITC-dextran as a plasma marker were intravenously injected, and pulsed laser was irradiated according to the method in Example <2-1>. Fluorescence of Hoechst 333342 and 2M-Da FITC-dextran was analyzed at a predetermined time after the laser irradiation.

As a result, not only blood vessel, but also astrocytes stained with fluorescence were observed around an irradiated region 2 hours after the laser irradiation, and the FITC-dextran image could be subtracted from the SR101 image to selectively visualize the astrocyte stained with SR101 (FIGS. 6a and 6b). No noticeable staining of SR101 was observed in a region in the cerebral hemisphere as a control group (FIG. 6c), suggesting that the astrocyte staining in the brain tissue was mediated by pulsed laser induced vascular permeabilization.

<4-3> Delivery of Nano Materials (Quantum Dot and Magnetic Oxide Nanoparticles (MION)) into the Brain Tissue According to the methods in Examples <4-1> and <4-2>, it was confirmed that nanoparticles quantum dot (Q21021MP, Invitrogen) and TAMRA conjugated magnetic oxide nanoparticle (MION) were delivered.

As a result, it was shown that nanoparticles quantum dot and MION were delivered into the brain tissue (FIG. 7), suggesting that induction of vascular permeablization by pulsed laser might be applicable to delivery of nanoparticles.

Example 5

Identification of Effects of Pulsed Laser on Vascular Permeabilization in Various Tissues In order to confirm the induction of vascular permeabilization in various tissues other than the central nervous system by pulsed laser, vascular permeabilization was observed in various tissues including meninges, skulls, striated muscles in the dorsal skin, and ears of mice. Meningeal vasculature was used in the thinned skull model in <Example 1>, and the scalp was removed to observe the skull. Striated muscles were used in a skin chamber model in the dorsal skin.

As a result, it was observed that 2M-Da FITC-dextran was locally and transiently extravasated into meninge, skull, striated muscle in the dorsal skin, and ear by a femtosecond pulsed laser irradiation (FIG. 8). Thus, it could be seen that induction of vascular permeabilization by pulsed laser might be applicable to the blood vessel of other various tissues as well as the brain blood vessel.

Because the pulsed laser of the present invention effectively induces vascular permeabilization, effectively delivers intravascular materials into tissues and minimizes insult to the tissues by the induced vascular permeabilization, and transiently and locally targets a subcutaneous tissue for non-invasive modulation due to its nonlinearity, it may be usefully used for a modulator of vascular permeability and modulation of permeability.

As described above, because the pulsed laser of the present invention has excellent induction effects on vascular permeabilization, it may be usefully used in development of modulators of vascular permeability and methods for modulating vascular permeability for reduced insult to blood vessel by pulse energy and noninvasive modulation due to its nonlinearity.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for increasing vascular permeabilization, the method comprising:
   1) intravascularly injecting a material to be delivered into an individual;
   2) targeting a vascular wall; and
   3) irradiating a pulsed laser on the targeted vascular wall, thereby increasing vascular permeability of said targeted vascular wall to allow passage of said material into surrounding tissue.

2. The method as set forth in claim 1, wherein the vascular wall in 2) is targeted by any one selected from the group consisting of confocal fluorescent imaging, multiphoton fluorescent imaging, and optical coherence tomography.

3. The method as set forth in claim 1, comprising observing physiological parameters.

4. The method as set forth in claim 3, wherein the physiological parameters are changes in vivo such as selected from the group consisting of degree of damage to blood vessel, blood flow, and vascular diameter.

5. The method as set forth in claim 1, wherein the pulsed laser in 3) is transmitted through an optical fiber.

6. The method as set forth in claim 1, wherein the pulsewidth of the pulsed laser is about 1 femtosecond to about 100 nanoseconds.

7. The method as set forth in claim 1, wherein the wavelength of the pulsed laser is about 700 nm to about 1000 nm.

8. The method as set forth in claim 1, wherein the repetition rate of the pulsed laser is about 1 MHz to about 100 MHz.

9. The method as set forth in claim 1, wherein the irradiance of the pulsed laser is a multiphoton ionization threshold to an optical breakdown threshold.

10. The method as set forth in claim 1, wherein the irradiation duration by the pulsed laser is about 100 ns to about 10 ms.

11. The method as set forth in claim 1, wherein the blood vessel is one present in at least one selected from the group consisting of the brain, retina, meningeal vasculature, skull vasculature, striated muscle in the dorsal skin, and ear.

* * * * *